United States Patent
Zimmermann et al.

(10) Patent No.: US 9,055,722 B2
(45) Date of Patent: Jun. 16, 2015

(54) PRODUCT FOR USE IN AGRICULTURE OR HORTICULTURE

(75) Inventors: Diane Zimmermann, Geneva (CH); Nathalie Nurdin, Geneva (CH); Eric Allemann, Geneva (CH); Eric Doelker, Geneva (CH); Robert Gurny, Geneva (CH); Eric van der Drift, Enkhuizen (NL); Ruud Scheffer, Almere (NL); Stefan Baum, Munchwilen (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 2001 days.

(21) Appl. No.: 10/496,188

(22) PCT Filed: Nov. 22, 2002

(86) PCT No.: PCT/US02/37548
§ 371 (c)(1),
(2), (4) Date: May 23, 2005

(87) PCT Pub. No.: WO03/045139
PCT Pub. Date: Jun. 5, 2003

(65) Prior Publication Data
US 2006/0162249 A1    Jul. 27, 2006

(30) Foreign Application Priority Data

Nov. 23, 2001 (GB) .................................. 0128134.4

(51) Int. Cl.
*A01C 1/06*    (2006.01)
*A01H 4/00*    (2006.01)

(52) U.S. Cl.
CPC ...................................... *A01H 4/006* (2013.01)

(58) Field of Classification Search
USPC .............................. 47/57.6; 504/100; 424/410
See application file for complete search history.

(56) References Cited

U.S. PATENT DOCUMENTS

| 4,583,320 A | 4/1986 | Redenbaugh |
| 4,779,376 A | 10/1988 | Redenbaugh |
| 5,236,469 A | 8/1993 | Carlson et al. |

*Primary Examiner* — Trinh Nguyen
(74) *Attorney, Agent, or Firm* — Brian D. McAlhaney

(57) ABSTRACT

The invention relates to a product for use in agriculture or horticulture comprising a capsule dissolving or disintegrating in the presence of humidity wherein at least a seed and a controlled release system comprising an agrochemical compound is located.

18 Claims, No Drawings

PRODUCT FOR USE IN AGRICULTURE OR HORTICULTURE

This application is a 371 of International Application No. PCT/US02/37548 filed Nov. 22, 2002, which claims priority to GB 0128134.4, filed Nov. 23, 2001, the contents of which are incorporated herein by reference.

The invention relates to a product for use in agriculture or horticulture and a method for manufacturing said product.

In order to prevent early attack of seeds or seedlings by insects or fungi, for example, seeds are often coated with agrochemical compounds. However, such coatings are always susceptible to cause delays in germination or emergence and the potential phytotoxicity of the agrochemical compound has to be taken in consideration. Additionally, such coatings target early attack while there will still be a need for further protection throughout the growing season.

Accordingly, an object of the invention is a product for use in agriculture or horticulture comprising a capsule wherein at least a seed and a controlled release system comprising an agrochemical compound is located.

The proposed product has the following advantages:
  it is very flexible; the ratio of controlled release system and seed can easily be varied; one or more controlled release systems can be incorporated; additional components may be incorporated like nutrients or fertilizers, for example;
  it is a closed system; there is no contact of the agrochemical compound with the user; viscous or liquid components may be used;
  it is easy to apply and may provide protection throughout a whole growing season.

The capsule useful for carrying out the invention may be a conventional capsule dissolving or disintegrating in the presence of humidity. Such capsules are, for example, used in medicinal arts to administer medicines. Such capsules may therefore be obtained using conventional techniques known in the art. As an indication, such capsules measure from 10 to 20 mm in length and have a diameter ranging from 3 to 8 mm, a preferred dimension being 15 mm in length and 5 mm in diameter. The ratio of length to diameter is usually from 2:1 to 4:1. The material of the capsule is chosen so that it dissolves or disintegrates in the presence of humidity. It is preferred that such dissolution or disintegration occurs rather rapidly. It is also preferred that the capsule is gas and water permeable so that germination is not hindered. Suitable materials for such capsules are, for example, gelatin, starch, hydroxypropylmethylcellulose and other cellulose derivatives. Preferred materials are starch and hydroxypropylmethylcellulose.

Seeds useful for carrying out the invention may be naked seeds or seeds coated according to known coating techniques. For example, the seeds may be vegetable seeds or flower seeds. Preferred seeds are vegetable seeds. Examples of vegetable seeds are those for cabbage, lettuce and sugar beet.

The controlled release system may be in form of a powder, granule, pellet, tablet, extrudate or any other form insuring the controlled release properties of the agrochemical compound. A preferred form of the controlled release system is a tablet. The tablet may be optionally coated with a polymer film coat. The controlled release system is, for example, a system which releases the agrochemical compound in a continuous manner over a prolonged period which may be several days to a whole growing season. Such controlled release system has to be contrasted by the conventional agrochemical formulations where all of the active ingredient is expected to be released immediately after application. Such controlled release may also take the form of no or very reduced initial release and a substantial release only after a certain period of time which may then be over a short period of time or in a prolonged way. Therefore, such controlled release system in form of a tablet, for example, does not need to be a homogeneous tablet but may comprise a core containing the agrochemical compound and a coating without such compound. In case of a controlled release system in form of an extrudate, an analogous configuration may be obtained by co-extrusion.

Typically, the controlled release system in form of a tablet comprises at least one agrochemical compound and a polymer, lipid or wax, either alone or in mixtures. In addition, the tablet may contain a variety of additives selected from the group consisting of diluents, lubricants, antiadherents and glidants. Some excipients can serve multiple purposes. The amount of the agrochemical compound in the controlled release system may vary widely. As an indication, the amount of the agrochemical compound is from 0.1 to 50% by weight of the controlled release system.

Examples of suitable polymer classes are ethylcellulose, cellulose acetate, cellulose acetate butyrate, polyhydroxybutyrate, polyacrylate, polymethacrylate, polyvinylchloride and polyhydroxybutyratelpolyhydroxyvalerate and others known in the art.

Examples of suitable lipidic ingredients are glyceryl palmitostearate, glyceryl tribehenate, stearic acid, stearyl alcohol and vegetable oil (e.g. canola, corn, cottonseed, sesame, soybean), hydrogenated vegetable oil (e.g. hydrogenated Cottonseed oil), vegetable wax and others known in the art.

Examples of suitable diluents or fillers are carbonates (calcium, magnesium), phosphates (calcium), sulfates (calcium), oxides (magnesium), chlorides (potassium, sodium), microcrystalline cellulose (e.g. Avicel™), starches, talc, kaolin, saccharides (dextrose, fructose, lactose, mannitol, sorbitol, sucrose) and others known in the art.

Examples of suitable lubricants are stearates (magnesium, calcium, zinc), glyceryl palmitostearate, glyceryl monostearate, lauryl sulfate, stearyl fumarate, talc, starches, stearic acid, hydrogenated vegetable oils (e.g. hydrogenated Cottonseed oil) and others known in the art.

Examples of suitable antiadherents are microcrystalline cellulose (e.g. Avicel™), colloidal silicon dioxide (e.g. Aerosil™), talc and others known in the art.

Examples of suitable glidants are powdered cellulose, magnesium trisilicate, colloidal silicon dioxide (e.g. Aerosil™), starches, talc and others known in the art.

The tablets useful in carrying out the invention may be obtained using conventional techniques. For example, after mixing, the components are compressed using conventional compression equipment, like a hydraulic press or a compression machine (eccentric or rotative).

The agrochemical compounds to be used in the instant invention include herbicides, fungicides and insecticides as well as plant growth regulators and inhibitors and plant activators. Preferred are agrochemical compounds which show systemic or mesostemic properties, which means such compounds are transported by the plant to different loci of the plant.

Examples of suitable herbicides are: Pretilachlor, Clomeprop, Bifenox, Pyrazoxyfen, Pyrazolynate, Cinosulfuron, Dimepiperate, Bensulfuron-methyl, Pyrazosulfuron-ethyl, Naproanilide, Bromobutide, Mefenacet, lmazosulfuron, Daimuron, Bentazon, Simetryn, Etobenzanid, Cyhalofop-butyl, Cafenstrole, Azimsulfuron, Pyriminobac-methyl, Benzofenap, Pyributicarb, Thenylchlor, MCPB, Benfuresate, Butamifos, Cyclosulfamuron, Dimethametryn, Esprocarb, Fentrazamide, Indanofan, Isoprothiolane, Molinate, Oxadiclomefon, Oxaziclomefone, Paclobutrazol, Pentoxazone, Prohexadione-ca, Pyrazogyl, Simetryne, Thiobencarb and Uniconazole.

Examples of suitable fungicides are: Acibenzolar-S-Methyl, Isoprothiolane, Ipconazole, Iprodione, Oxolinic acid, Kasugamycin, Capropamid, Captan, Thiabendazole, Thiram, Thiophanate-methyl, Organocopper, Tricyclazole, Triflumizole, Validamycin, Azoxystrobin, Pyroquilon, Fludioxonil, Prochloraz, Probenazole, Benomyl, Methasulfocarb, TPN, BJL-002, BJL-003, Chlorothalonil, Copper, Diclocymet, Diclomezine, Edifenphos, Fenoxanil, Ferimzone, Flutolanil, Furametpyr, Hymexazol, Mepronil, Metominostrobin, Pefurazoate, Pencycuron, Tecloftalam and Thifluzamide.

Examples of suitable insecticides are: Imidacloprid, Etofenprox, Cartap, Thiamethoxam, Thiocyclam, Bensultap, Bendiocarb, Monocrotophos, Alprocarb, Pymetrozine, Benfuracarb, Buprofezin, Carbosulfan, Cycloprothrin, Fenitrothion, Fipronil, Isoxathion, Phenthoate, Silafluofen, Triazophos, Trichlorfon, Methoxyfenozide and Clothianidin.

Among these agrochemical compounds, Acibenzolar-S-methyl, Fludioxonil, Pyroquilon, Thiamethoxam, Thiocyclam, Pymetrozine, Preblachlor, Cinosulfuron are particularly preferred.

A further aspect of the invention is the combination of two or more controlled release systems. Such release systems may comprise the same or different agrochemical compound and exhibit the same or different release profiles.

A further aspect of the invention is the addition of a further component into the capsule. Such further component may, for example, be a nutrient or fertilizer. Such further component may also be a further agrochemical compound. Such further component may be a solid but also a viscous or liquid component.

A further aspect of the instant invention is a method for manufacturing a product as herein described characterized that within a capsule is placed at least one seed and at least one controlled release system whereafter the capsule is closed. The method may include or have added as a further step that the capsule is sealed. The preferred embodiments for the product apply in analogy to the method.

The specific examples set forth below further illustrate the invention.

EXAMPLE 1

A-Tablets and B-Tablets

This example shows how to manufacture units of a controlled release formulation in matrix tablet form containing 0.2 mg of thiamethoxam.

After individual sieving to ensure small particle size (less than 400 μm), 0.53% (w/w) of thiamethoxam, 98.97% (wtw) of cellulose acetate (CA 398-10, Eastman, USA) and 0.4% (w/w) of Aerosil® 200 (Degussa AG, Germany) are thoroughly mixed in appropriate amounts in a planetary blender (Turbula, model T2A, W.A. Bachofen, Switzerland) for 15-20 minutes. Magnesium stearate (0.1% w/w) is then added and the powder further mixed for 3 more minutes. The tablets (nominal weight: 39±1 mg) are prepared by direct compression using a laboratory eccentric press (Korsch, model EK-O, Bauknecht, Germany) with flat 5 mm-diameter punches at variable compression forces, preferably between about 140 MPa to about 270 MPa. For the so-called A-tablets, the compression force has been typically set to 150 MPa and for the B-tablets to 260 MPa.

EXAMPLE 2

This example shows how to manufacture units of a controlled release formulation in matrix tablet form containing 0.8 mg of thiamethoxam.

Following the same procedure as for Example 1, a powdery mixture consisting of 2.1% (w/w) thiametoxam, 87.4% (w/w) cellulose acetate (CA 398-10, Eastman), 10% (w/w) stearic acid, 0.4% (w/w) aerosil and 0.1% (w/w) magnesium stearate is compacted into tablets (nominal weight: 39±1 mg).

EXAMPLE 3

C-Tablets

This example shows how to manufacture units of a controlled release formulation in coated tablet form containing 0.2 mg of thiamethoxam.

Following the same procedure as for Example 1, a powdery mixture consisting of 0.53% (w/w) thiametoxam, 58.97% (w/w) cellulose acetate (CA 398-10, Eastman), 40% (w/w) lactose, 0.4% (w/w) aerosil and 0.1% (w/w) magnesium stearate is compacted into tablet cores (nominal weight: 39±1 mg) using convex punches. A coating solution formed of a mixture of acrylate and methacrylate copolymers (commercially available as Eudragit RS 30 D and Eudragit RL 30 D, Röhm GmbH, Germany) is sprayed on the cores.

Coating formulations are prepared as follows: the 30% water-dispersion of commercially available Eudragit (either RS 30 D alone or in 85/15, 92/8 mixtures with RL 30 D) is half-diluted with purified water containing the plasticizer (triethyl citrate, 15% w/w of the dry polymer) in order to achieve a final dry polymer content of 15% in the dispersion. The mixture is gently stirred for 30 min prior to use.

For the so-called C-tablets, the coating solution consisted of 42.5% (w/w) Eudragit RS 30 D (30% suspension), 7.5% (w/w) Eudragit RL 30 D (30% suspension), 2.25% (w/w) triethylcitrate and 47.75% (w/w) water.

A load of convex tablets (70-200 g) is introduced in a laboratory-scale fluidized bed apparatus equipped with a bottom-spray system. A stream of drying air is applied and the cores are heated until stabilisation of the inlet/outlet temperatures is achieved (15-20 min). The acrylic water-based dispersion is delivered to the cores. Samples are taken at different coating times for characterisation and dissolution studies. A 5 min drying period is observed between each nebulisation cycle. Coating application is continued until an approximate 40-45% tablet weight gain is achieved. At the end of the process, the tablets are further dried at the same temperature for 20-25 minutes. Specific process parameters depend on the equipment used and should be carefully adjusted to obtain optimum tablet circulation, appropriate polymer distribution and effective film forming conditions.

EXAMPLE 4

Germination Tests

Hydroxypropylmethylcellulose capsules (Capsugel, size 2), length 15 mm, diameter 5 mm are used. The capsules are filled with naked cabbage seeds and A- or B-tablets. The dose of active ingredient is varied by adding different quantities of A- or B-tablets into one capsule. The samples (2*25 seeds) are germinated on paper at a temperature of 15° C.

At day 3, the total number of germinated seeds is counted and reported in Table 1. At day 7, the number of normal plants is counted and reported in Table 1.

TABLE 1

| Test No. | treatment | germination 3 d [%-total] | germination 7 d [%-normal] |
|---|---|---|---|
| 100 | none | 98 | 96 |
| 101 | capsule | 100 | 86 |
| 102 | coated 0.4 mg ai/seed | 70 | 14 |
| 103 | coated 1.2 mg ai/seed | 66 | 0 |
| 104 | capsule 0.4 mg ai/seed, A-tablet | 100 | 30 |
| 105 | capsule 0.4 mg ai/seed, B-tablet | 100 | 54 |
| 106 | capsule 1.2 mg ai/seed, A-tablet | 100 | 28 |
| 107 | capsule 1.2 mg ai/seed, B-tablet | 100 | 48 |

Test Nos. 100 to 103 are for comparison. Test Nos. 104-107 are according to the invention.

At day 3, all seeds except the coated seeds have germinated. At day 7, the tests with the seeds in the capsules show a significant higher amount of normal plants compared to the coated seeds.

EXAMPLE 5

Germination Tests

Hydroxpropylmethylcellulose capsules (Capsugel, size 2), length 15 mm, diameter 5 mm are used. The capsules are filled with naked cabbage seeds and A- or B-tablets. The dose of active ingredient is varied by adding different quantities of A- or B-tablets into one capsule. The samples (2*25 seeds) are germinated on soil covered with sieved soil at a temperature of 18° C.

At day 14 the number of normal plants is counted and reported in Table 2.

TABLE 2

| Test No. | treatment | germination 14 d [%-normal] |
|---|---|---|
| 100 | none | 100 |
| 101 | capsule | 88 |
| 102 | coated 0.4 mg ai/seed | 78 |
| 103 | coated 1.2 mg ai/seed | 0 |
| 104 | capsule 0.4 mg ai/seed, A-tablet | 94 |
| 105 | capsule 0.4 mg ai/seed, B-tablet | 100 |
| 106 | capsule 1.2 mg ai/seed, A-tablet | 100 |
| 107 | capsule 1.2 mg ai/seed, B-tablet | 100 |

Test Nos. 100 to 103 are for comparison. Test Nos. 104-107 are according to the invention.

At day 14, the tests with the seeds in the capsules according to the invention show a significant higher amount of normal plants compared to the coated seeds.

The invention claimed is:

1. An article of manufacture for use in agriculture or horticulture comprising:
   a capsule which dissolves or disintegrates in the presence of humidity; and
   at least a seed and a controlled release system comprising an agrochemical compound located within the capsule,
   wherein said capsule prevents exposure to said agrochemical compound prior to dissolving or disintegrating of said capsule.

2. The article according to claim 1, wherein the capsule measures from 10 to 20 mm in length and has a diameter ranging from 3 to 8 mm.

3. The article according to claim 1, wherein the capsule comprises a capsule material comprising starch or hydroxypropylmethylcellulose.

4. The article according to claim 1, wherein the seed is a vegetable or a flower seed.

5. The article according to claim 1, wherein the controlled release system is a system that releases the agrochemical compound in a continuous manner over a prolonged period of time.

6. The article according to claim 1, wherein the controlled release system comprises 0.1 to 50% by weight of the agrochemical compound.

7. The article according to claim 1, wherein the agrochemical compound is selected from Acibenzolar-S-methyl, Fludioxonil, Pyroquilon, Thiamethoxam, Thiocyclam, Pymetrozine, Pretilachlor and Cinosulfuron.

8. The article according to claim 1, wherein the capsule measures from 10 to 20 mm in length and has a diameter ranging from 3 to 8 mm, the capsule comprises a capsule material comprising starch or hydroxypropylmethylcellulose, the seed is a vegetable or a flower seed, the controlled release system comprises 0.1 to 50% by weight of the agrochemical compound, and the agrochemical compound is selected from Acibenzolar-S-methyl, Fludioxonil, Pyroquilon, Thiamethoxam, Thiocyclam, Pymetrozine, Pretilachlor and Cinosulfuron.

9. The article according to claim 1, wherein said capsule comprises a capsule material that is gas and water permeable.

10. The article according to claim 1, wherein said controlled release system further comprises a polymer, a lipid, a wax, or mixtures.

11. The article according to claim 10, wherein said controlled release system further comprises one or more additives selected from the group consisting of diluents, lubricants, anti-adherents and glidants.

12. The article according to claim 11, wherein said controlled release system comprises cellulose acetate and colloidal silicone dioxide.

13. An article of manufacture for use in agriculture or horticulture comprising:
    a core comprising at least a seed and a controlled release system comprising an agrochemical compound; and
    a capsule completely encapsulating said core,
    wherein said capsule comprises a capsule material that (i) dissolves or disintegrates in the presence of humidity, (ii) is gas and water permeable, and (iii) prevents exposure to said agrochemical compound prior to dissolving or disintegrating.

14. The article according to claim 13, wherein said capsule material comprises starch or hydroxypropylmethylcellulose.

15. The article according to claim 13, wherein said capsule material consists of starch or hydroxypropylmethylcellulose.

16. The article according to claim 13, wherein said core further comprises a nutrient, a fertilizer, a second agrochemical compound, or a combination thereof.

17. An article of manufacture for use in agriculture or horticulture comprising:
    a capsule comprising a single capsule material that (i) dissolves or disintegrates in the presence of humidity, (ii) is gas and water permeable, and (iii) prevents exposure to said agrochemical compound prior to dissolving or disintegrating; and
    at least a seed and at least one controlled release system with each controlled release system comprising an agrochemical compound located within and completely encapsulated by the single capsule material.

18. The article according to claim 17, wherein said single capsule material completely encapsulates two or more controlled release systems with each controlled release system comprising the same agrochemical compound or a different agrochemical compound.

* * * * *